United States Patent
Wu et al.

(10) Patent No.: US 11,490,697 B2
(45) Date of Patent: Nov. 8, 2022

(54) CONSISTENTLY-TIGHT WATCH BAND

(71) Applicant: Apple Inc., Cupertino, CA (US)

(72) Inventors: Yiwen Wu, Stanford, CA (US); Erik G. de Jong, San Francisco, CA (US); Colin M. Ely, Sunnyvale, CA (US); Sameer Pandya, Sunnyvale, CA (US)

(73) Assignee: Apple, Inc., Cupertino, CA (US)

( * ) Notice: Subject to any disclaimer, the term of this patent is extended or adjusted under 35 U.S.C. 154(b) by 528 days.

(21) Appl. No.: 16/591,511

(22) Filed: Oct. 2, 2019

(65) Prior Publication Data
US 2020/0029660 A1    Jan. 30, 2020

Related U.S. Application Data

(63) Continuation of application No. 15/269,710, filed on Sep. 19, 2016, now Pat. No. 10,455,906.

(51) Int. Cl.
*A44C 5/00* (2006.01)
*A44C 5/02* (2006.01)
*A61B 5/00* (2006.01)
*A61B 5/024* (2006.01)

(52) U.S. Cl.
CPC ............ *A44C 5/0069* (2013.01); *A44C 5/027* (2013.01); *A61B 5/02438* (2013.01); *A61B 5/681* (2013.01)

(58) Field of Classification Search
CPC ........... A44C 5/00; A44C 5/0069; A44C 5/02; A44C 5/027; A44C 5/10; A44C 5/14; A44C 5/18; A44C 5/20; A44B 11/24; A05K 5/00; A05K 5/0086
See application file for complete search history.

(56) References Cited

U.S. PATENT DOCUMENTS

| | | | |
|---|---|---|---|
| 1,622,769 A | 3/1927 | Coombs | |
| 2,564,652 A | 8/1951 | Templeman | |
| 3,063,058 A | 11/1962 | Vollet | |
| 3,488,565 A * | 1/1970 | Teltscher | G04B 47/00 968/398 |
| RE28,793 E * | 5/1976 | Bert | A44C 5/14 224/164 |
| 6,406,177 B1 * | 6/2002 | Fukushima | A44C 5/10 59/901 |
| 2008/0058620 A1 | 3/2008 | Lee et al. | |
| 2014/0135612 A1 | 5/2014 | Yuen et al. | |

(Continued)

OTHER PUBLICATIONS

NPL Search (Apr. 4, 2022).*

*Primary Examiner* — Van T Trieu
(74) *Attorney, Agent, or Firm* — BakerHostetler

(57) ABSTRACT

A watch band is disclosed. The watch band maintains a substantially constant tension throughout changes in its length while worn by a user. Such changes in length may occur automatically to accommodate changes in the size and circumference of a user's wrist as they move their wrist normally. By maintaining a constant tension, the watch band also maintains a constant force on the user's wrist, and causes a watch body attached to the watch band to also maintain a constant force on the user's wrist. This can increase a user's comfort, since the watch will not get tighter or constrict their wrist as they straighten and bend their wrist. It can also help optimize operation of any sensors in the watch band or watch body that benefit from being held against the user's wrist with a constant force, such as some physiological sensors.

20 Claims, 11 Drawing Sheets

(56) References Cited

U.S. PATENT DOCUMENTS

| | | | |
|---|---|---|---|
| 2014/0268522 A1* | 9/2014 | Tanaka | A61B 5/0295 361/679.01 |
| 2015/0157262 A1 | 6/2015 | Schuessler | |
| 2015/0265214 A1 | 9/2015 | De Kok et al. | |
| 2016/0015136 A1 | 1/2016 | Yue et al. | |
| 2016/0037866 A1* | 2/2016 | Rohrbach | A44C 5/14 2/170 |
| 2016/0071408 A1 | 3/2016 | Jiao et al. | |

\* cited by examiner

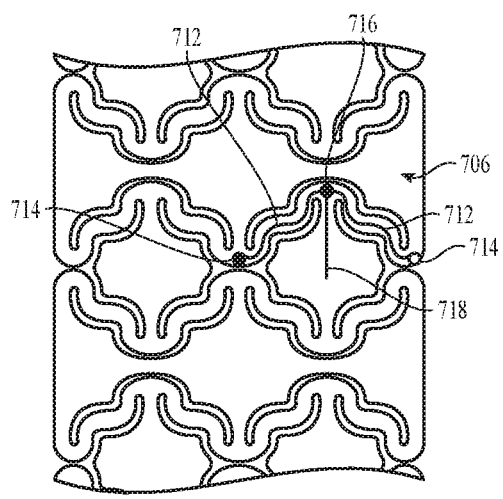
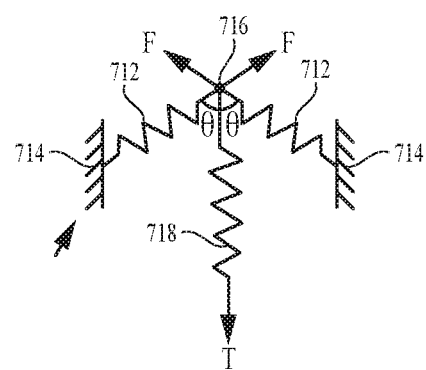
*FIG. 13*
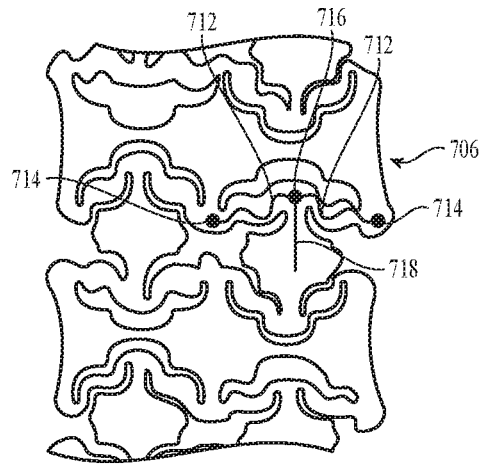
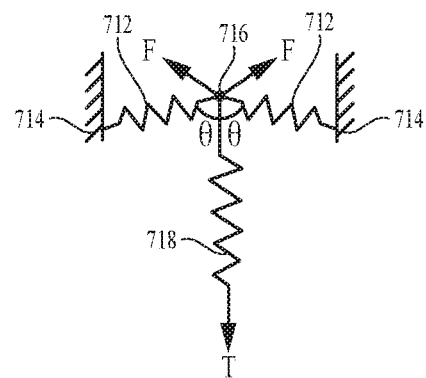
*FIG. 14*
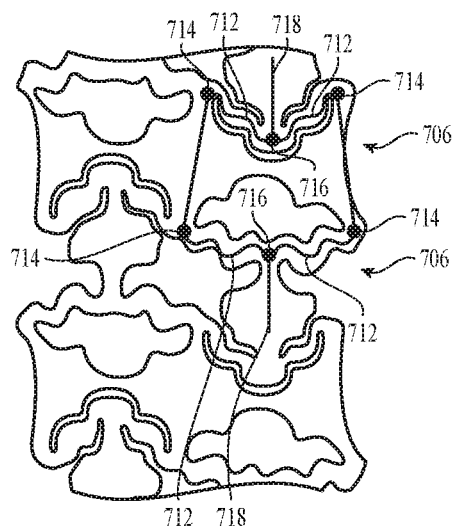
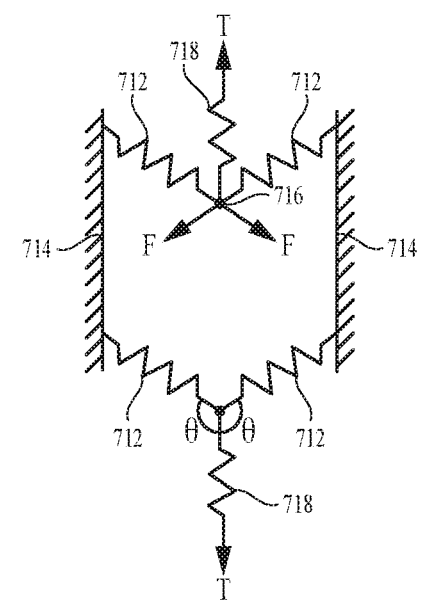
*FIG. 15*

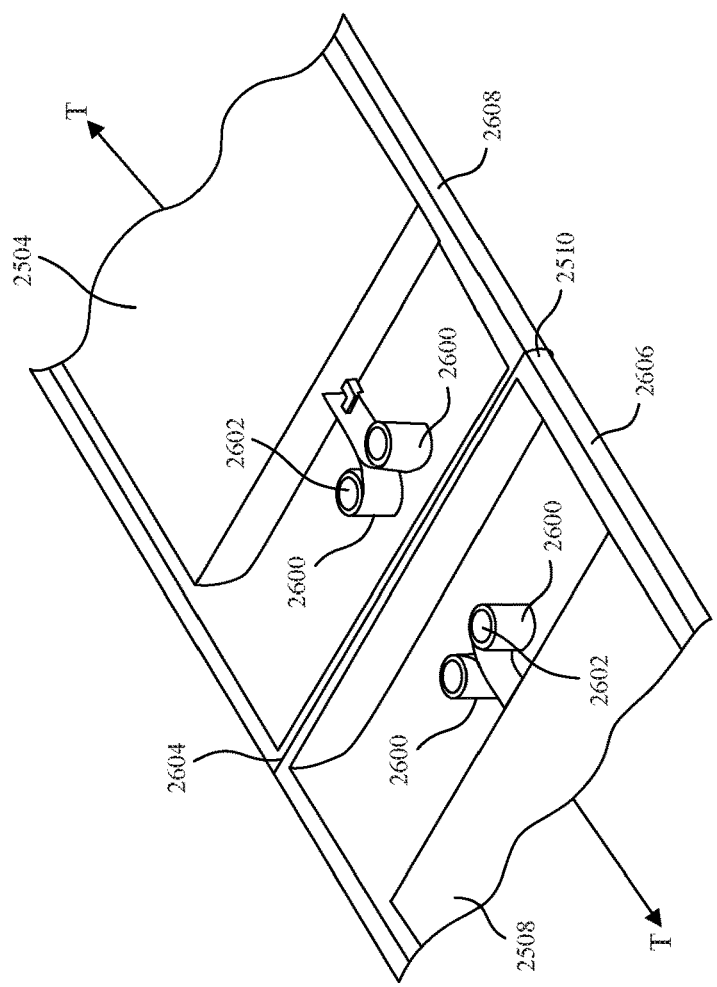
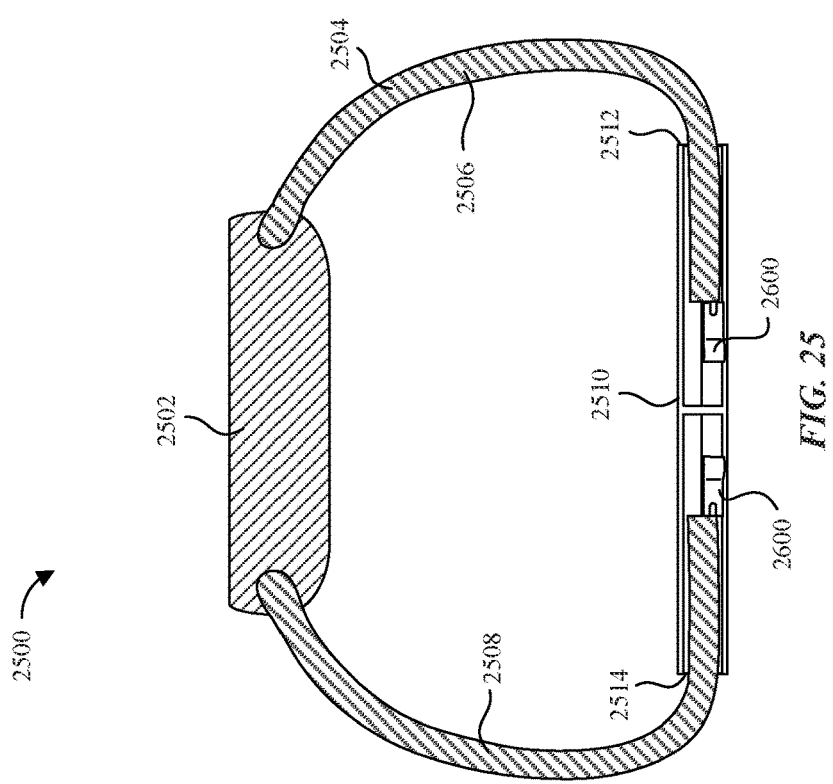

US 11,490,697 B2

CONSISTENTLY-TIGHT WATCH BAND

CROSS-REFERENCE TO RELATED APPLICATION

This application is a continuation of U.S. patent application Ser. No. 15/269,710, filed Sep. 19, 2016, the disclosure of which is hereby incorporated herein by reference in its entirety.

FIELD

The described embodiments relate generally to watch bands. More particularly, the present embodiments relate to watch bands that maintain a substantially constant tension when worn.

BACKGROUND

Watch bands may become tight around a user's wrist as the user moves their wrist. Such tightening can be uncomfortable.

SUMMARY

The present disclosure describes watch bands that maintain a substantially constant tension despite changes in their lengths while worn by a user. Such changes in length may occur automatically to accommodate changes in the size and circumference of a user's wrist as they move their wrist normally (e.g., moving it from straight, with a smaller circumference, to bent, with a larger circumference). By maintaining a constant tension, the watch bands may also maintain a constant force on the user's wrist, and they may cause a watch body attached to the bands to also maintain a constant force on the user's wrist. This can increase a user's comfort, since the watch will not get tighter or constrict their wrist as they straighten and bend their wrist. It can also help optimize operation of any sensors in the watch band or watch body that benefit from being held against the user's wrist with a constant force, such as some physiological sensors (e.g., some heart rate sensors).

Some embodiments of the watch band include repetitive compliant mechanisms that are each movable between a closed and an open position, and which move between the closed and open positions sequentially. The repetitive compliant mechanisms may themselves form the watch band, or at least the expandable portion of it. Each repetitive compliant mechanism may only insubstantially and temporarily change the tension in the overall band as it moves between the open and closed position, so the overall tension in the watch band remains substantially constant.

Other embodiments of the watch band include separate band portions that are movable relative to each other. The separate band portions may be connected together to form the watch band by constant-force springs. So when a user moves the portions away from each other or together by bending or straightening their wrist, the overall length of the watch band changes to accommodate the wrist, but the constant-force springs between the moving band portions maintain a constant overall tension in the watch band.

BRIEF DESCRIPTION OF THE DRAWINGS

The disclosure will be readily understood by the following detailed description in conjunction with the accompanying drawings, wherein like reference numerals designate like structural elements, and in which:

FIGS. 13-15 show a portion of the watch band of FIG. 7 as the repetitive compliant mechanisms open, alongside diagrammatic representations of the portion.
FIG. 25 shows a representative cross-section of a watch with a watch band that includes an expansion housing connected to watch band portions by constant-force springs.
FIG. 26 shows a detailed view of the expansion housing of FIG. 26.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the claims.

The following disclosure relates to a watch band that can maintain a substantially constant force while changing its length. For instance, when a wearer bends their wrist, the watch band may expand to accommodate the larger circumference of a bent wrist and may apply the same force to the user's wrist while doing so. This can increase the user's comfort, since the band expands with the user's wrist without applying greater force, rather than constricting or pinching the wrist or getting tighter as some non-extendable watch bands would. It can also help the watch perform optimally for functions that depend on a substantially constant force against the user's wrist. For example, some physiological sensors of the watch may benefit from being held against the user's wrist at a substantially constant force.

In a particular embodiment, a watch band may be formed with a pattern of discontinuities through itself. The discontinuities may allow portions of the band to separate and move away from each other as the band is extended. The discontinuities may form spring-like segments that compress past an inflection point to individually expand discrete segments of the band in a sequence. These segments may be tuned to allow for extension and contraction of the watch band while maintaining a substantially constant tension in the band.

In some other embodiments, a watch band may include a mechanism including constant-force springs connecting portions of the band. These constant-force springs can allow the portions of the band to move relative to each other while maintaining a substantially constant tension in the band.

In still other embodiments, a watch band may include a compressible pillow along its interior circumference that can compress to increase the interior circumference. This can operate as an effective expansion of the band as the available area within it is increased, such as to accommodate the change in circumference of a user's wrist within the band circumference. The compressible pillow may be formed of compressible foam, for example, or may be a bladder valved to maintain a substantially constant pressure.

These and other embodiments are discussed below with reference to the figures. However, those skilled in the art will readily appreciate that the detailed description given herein with respect to these figures is for explanatory purposes only and should not be construed as limiting.

Figure 1:
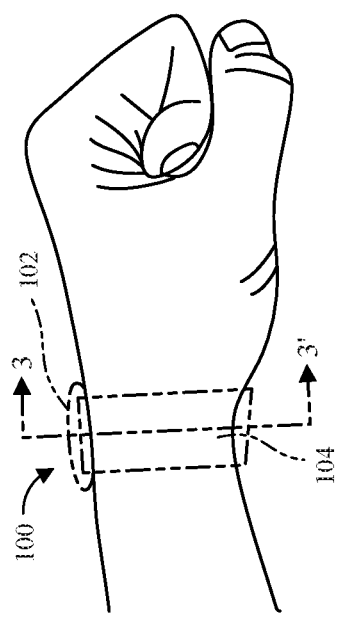
FIG. 1 shows a watch worn on a straight wrist of a user.
Figure 2:
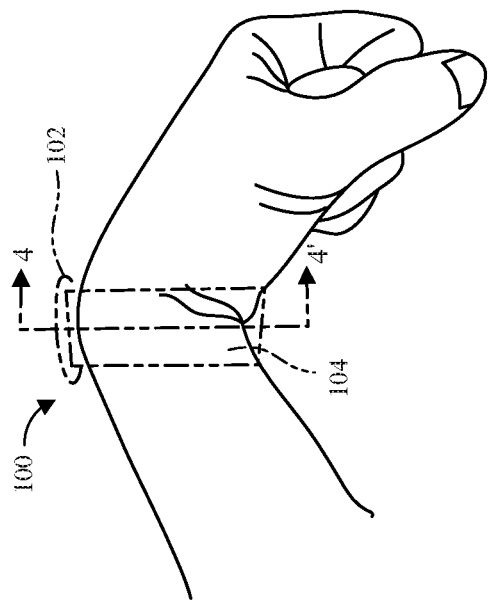
FIG. 2 shows a watch worn on a bent wrist of a user.

FIG. 1 illustrates a watch 100 in phantom lines worn on a wrist of a user. Watch 100 has a watch body 102 held on the wrist by a watch band 104, which is connected to watch body 102 at opposing ends of watch band 104. In FIG. 1 the user's wrist is in a neutral, straight position. FIG. 2 shows the user's wrist in a bent position. In the bent position the user's wrist around which watch band 104 extends becomes larger, increasing its circumference.

Figure 3:
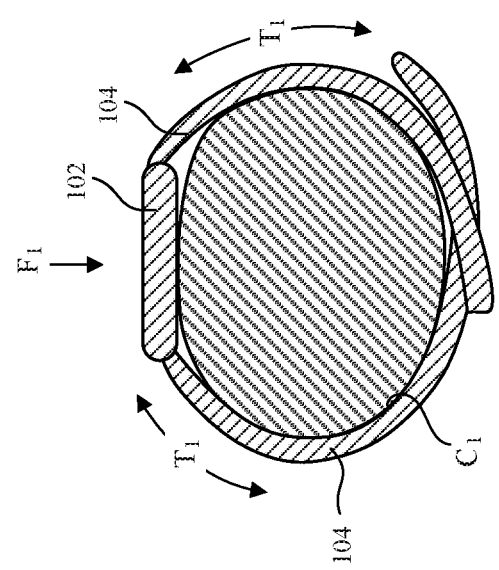
FIG. 3 shows a cross section taken through line 3-3' of FIG. 1
Figure 4:
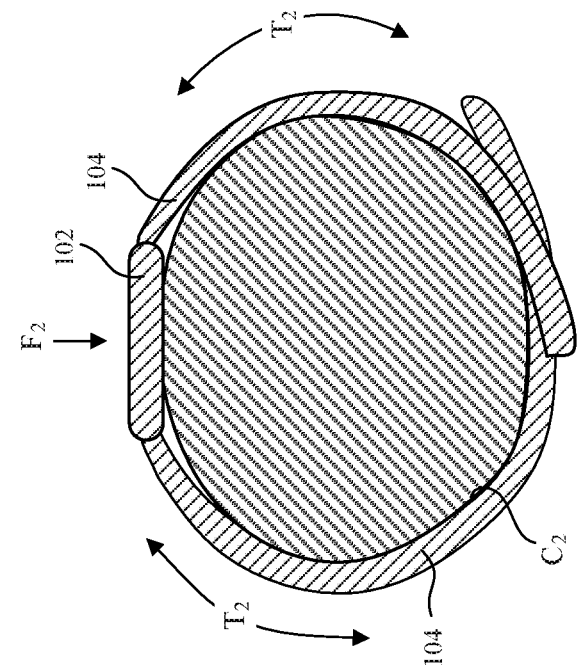
FIG. 4 shows a cross section taken through line 4-4' of FIG. 2.

The change in size of the user's wrist between the straight and bent positions is represented in FIGS. 3 and 4. FIG. 3 shows a cross-section through watch 100 on the user's wrist in the neutral, straight position, taken along line 3-3' of FIG. 1. In this position watch band 104 around the wrist has a circumference $C_1$, which corresponds to the circumference of the straight wrist due to its contact with the wrist throughout most of its length. Watch band 104 may be in tension $T_1$, which applies a force $F_1$ from watch body 102 to the wrist.

FIG. 4 shows a cross-section through watch 100 on the user's wrist in the bent position, taken along line 4-4' of FIG. 2. In this position the wrist becomes larger due to natural physiology: when the wrist bends, lower tendons tighten and compact the lower portion of the wrist, increasing its circumference at the area of watch 100. Watch band 104 around the wrist experiences a similar increase in circumference (to circumference $C_2$) to accommodate the larger wrist.

Figure 5:
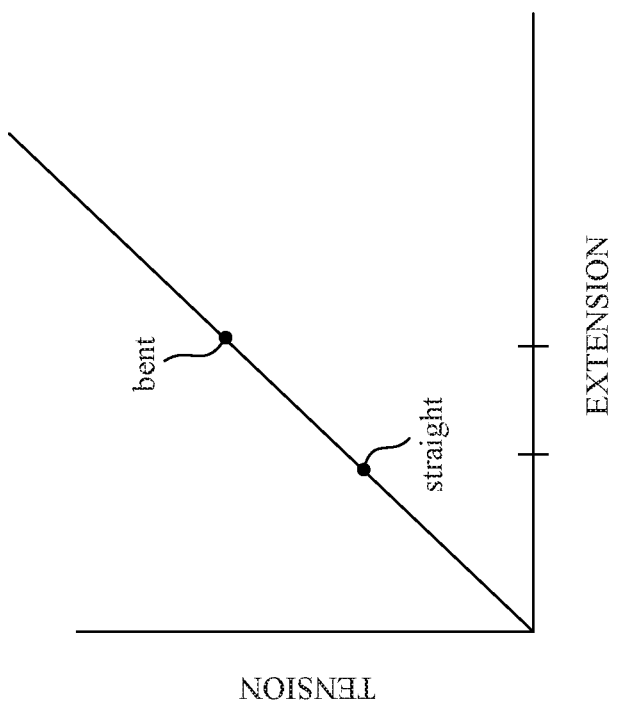

A non-extendable watch band may prevent or limit a user from moving their wrist from the straight to the bent position, or may cause discomfort when doing so, as the watch band may simply tighten around the wrist. An extendable watch band that stretches its material may allow movement from straight to bent, but may get tighter and tighter as the wrist's size increases. For example, if watch band 104 is such an extendable watch band, the tension in watch band 104 may increase to tension $T_2$, which is substantially higher than $T_1$, as represented by the linear tension-extension curve of the graph in FIG. 5. The force applied by watch body 102 may similarly increase to force $F_2$, which is substantially higher than $F_1$. Since a watch band that is too tight is more uncomfortable than a watch band that is too loose, the tendency of a watch band to tighten as a user moves their wrist may encourage the user to wear their watch loosely. A loose-fitting watch may degrade the usefulness of sensors in the watch that rely on contact with the wrist (e.g., physiological sensors such as heart rate sensors). A loose-fitting watch may also be uncomfortable to wear.

Embodiments of the present invention maintain a substantially constant tension in watch band 104 (e.g., such that $T_2$ is substantially the same as $T_1$) even as watch band 104 changes length (i.e., as the distance along the watch band between its ends increases or decreases) through a predetermined range (e.g., changes by at least 10 millimeters). The change in length may accommodate a wrist's change in size through the wrist's range of motion, and may be driven by the change in size of the wrist. The substantially constant tension in watch band 104 maintains a substantially constant force applied by watch band 104 to the user's wrist (e.g., such that F2 is substantially the same as F1), thereby increasing the user's comfort, improving performance of sensors, and encouraging optimal band tightness around the wrist.

Figure 6:
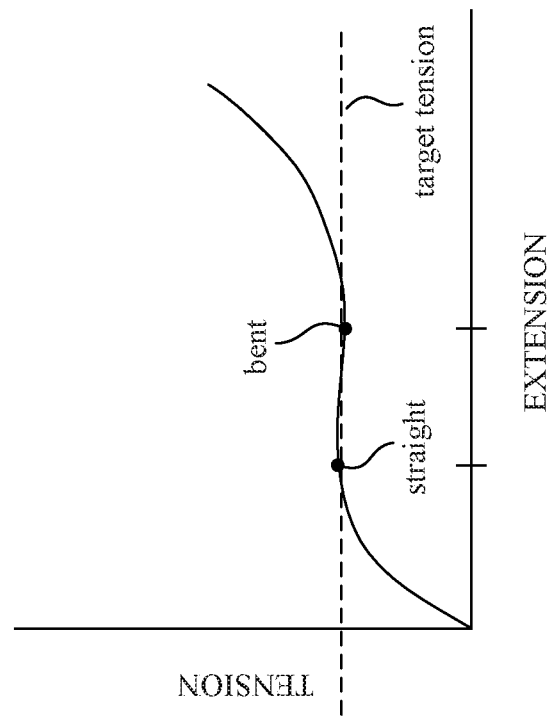
FIGS. 5 and 6 show tension-extension curves for watch bands.

FIG. 6 shows an exemplary tension-extension curve for such constant-force watch bands 104 as described herein. As shown, throughout the range of motion between a straight wrist and a bent wrist, watch band 104 maintains a substantially constant tension. The substantially constant tension may coincide with a predetermined target tension at which comfort and sensor performance are optimized.

As used herein, substantially constant tension or substantially the same tension refers to tension that changes or is different by less than 0.5 Newtons (e.g., less than 0.2 Newtons). As used herein, substantially constant force or substantially the same force refers to a force that changes or is different by less than 0.5 Newtons (e.g., less than 0.2 Newtons).

Figure 7:
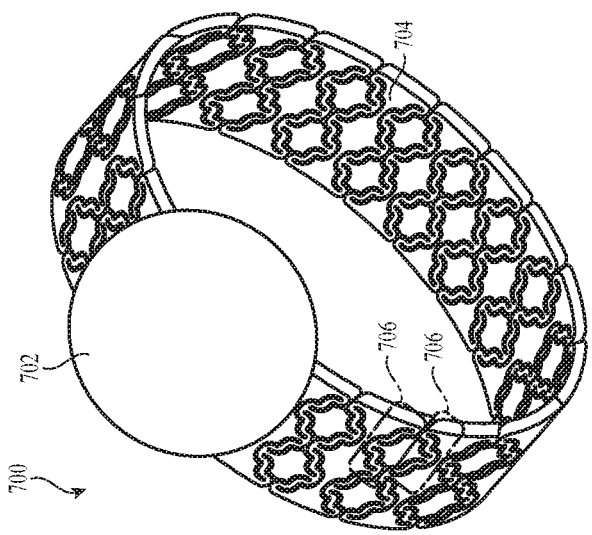
FIG. 7 shows a watch with a watch band that includes repetitive compliant mechanisms.

FIG. 7 shows a watch 700, which includes a watch body 702 coupled to a constant-force watch band 704. When worn, constant-force watch band 704 maintains a substantially constant tension and applies a substantially constant force to a wearer's wrist throughout changes in circumference of the wrist, as described above. Watch band 704 accomplishes this through repetitive compliant mechanisms 706, which form at least a portion of the length of watch band 704.

Figure 8:
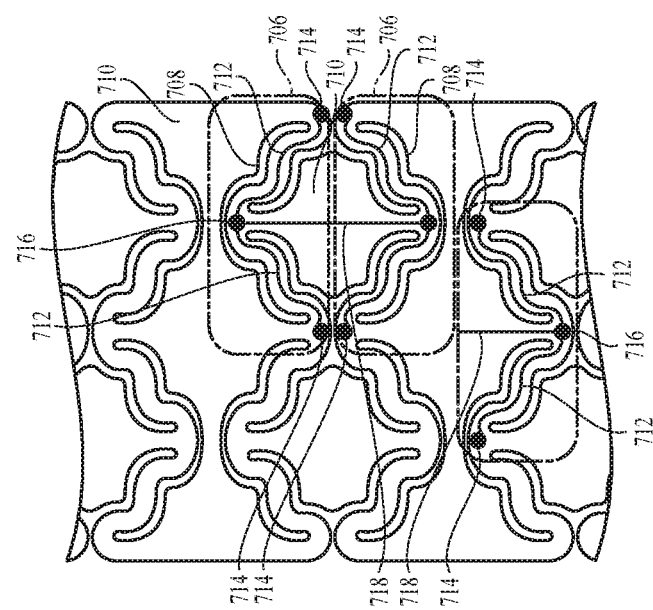
FIG. 8 shows a portion of the watch band of FIG. 7.

Watch band 704 is shown flat in FIGS. 8-15 to better explain its operation; however the operation described applies to watch band 704 when coupled to watch body 702 and worn by a user. FIG. 8 shows an enlarged view of a portion of watch band 704, which includes multiple repetitive compliant mechanisms 706. Repetitive compliant mechanisms 706 are formed by discontinuities 708 through a substance 710 of watch band 704, which allow portions of substance 710 to move relative to each other as watch band 704 lengthens or shortens. Substance 710 may be an elastomer, and repetitive compliant mechanisms 706 may be formed monolithically together of substance 710. In some embodiments, watch band 704 is formed entirely of the same material (e.g., a monolithic elastomer), which can simplify manufacturing (e.g., through injection molding).

Each repetitive compliant mechanism 706 includes a pair of opposing spring segments 712. Each opposing spring segment 712 extends from a ground joint 714 to a pivot joint 716. Pivot joint 716 may be connected to a pivot joint 716 of an adjacent repetitive compliant mechanism by a link 718.

Repetitive compliant mechanisms 706 may overlap. For example, a pivot joint 716 for one repetitive compliant mechanism 706 may be a ground joint 714 for an adjacent overlapping repetitive compliant mechanism 706 that shares a spring segment 712, as shown in FIG. 8. Such overlapping repetitive compliant mechanisms 706 may be oppositely-oriented to each other. Such overlapping repetitive compliant mechanisms are shown in FIG. 8, but not separately diagrammed or numbered, for clarity.

FIGS. 9-12 show a lengthening of watch band 704 under substantially constant tension. As the length of watch band 704 increases from FIG. 9 to FIG. 12 (length $L_1$>length $L_2$>length $L_3$>length $L_4$) its density per unit length may decrease, but corresponding tensions T remain substantially constant. Maximum and average width W of watch band 704 also remains substantially constant. As used herein, substantially constant width or substantially the same width refers to width that changes or is different by less than 5 millimeters (e.g., less than 2 millimeters).

Figure 9:
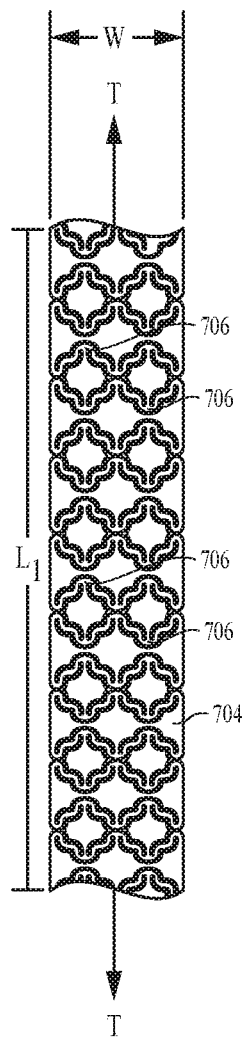
FIGS. 9-12 show the watch band of FIG. 7 at different lengths.
Figure 10:
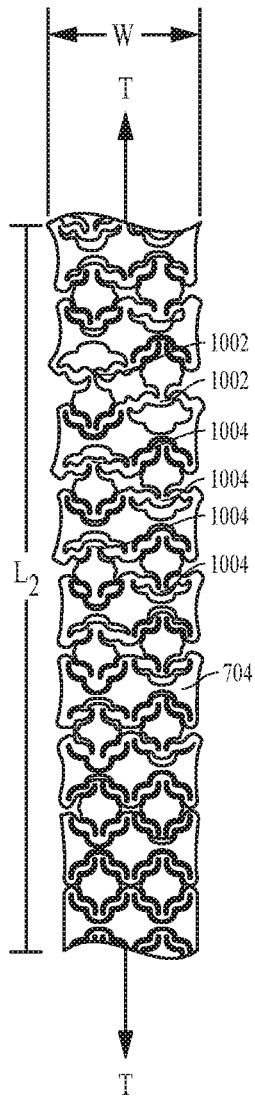
Figure 11:
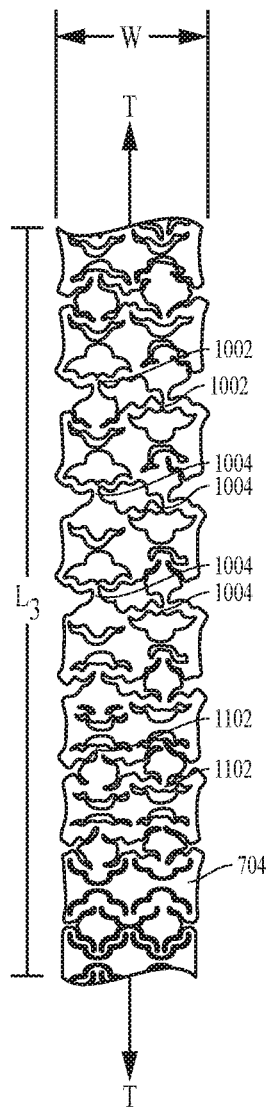
Figure 12:
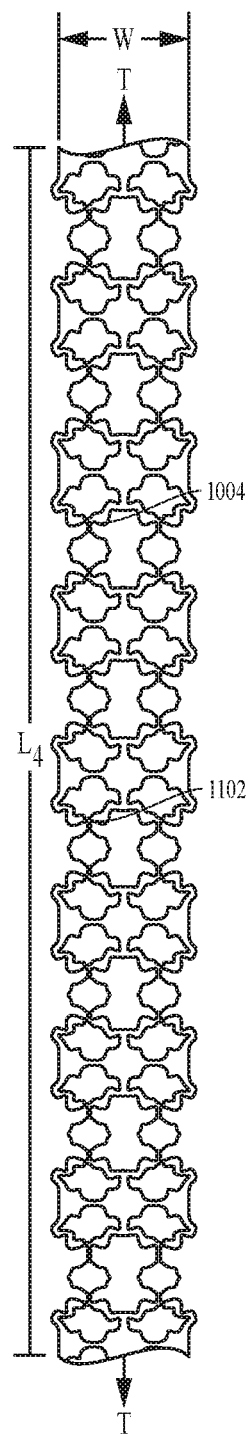

Maintaining substantially constant tension and width through substantial change in length (e.g., greater than 10 millimeters) is accomplished through the sequential extension of repetitive compliant mechanisms 706. As shown in FIG. 9, each repetitive compliant mechanism begins in a closed non-extended position. As length increases in FIG. 10, some repetitive compliant mechanisms 1002 have opened to an extended position, while other repetitive compliant mechanisms 1004 are in the process of moving to the open extended position. As length increases in FIG. 11, repetitive compliant mechanisms 1004 have opened and still other repetitive compliant mechanisms 1102 have begun to open. This process repeats with additional repetitive compliant mechanisms 706 until lengthening stops or until all repetitive compliant mechanisms have opened, as shown in FIG. 12. By opening sequentially (i.e., not all simultaneously), any small increase in tension attributable to the movement of a repetitive compliant mechanism 706 between positions is fleeting and unnoticeable, and maintains the overall tension on watch band 704 substantially constant.

FIGS. 13-15 show enlarged views of the transition of a repetitive compliant mechanism 706 from the non-extended (closed) position to the extended (open) position, alongside diagrammatic representations of their operation. As watch band 704 lengthens, repetitive compliant mechanism 706 transitions from the non-extended position of FIG. 13 to the intermediate position of FIG. 14. In this transition, forces F of spring segments 712 increase against each other and tension T on link 718 increases a small amount—not enough to raise the overall tension on watch band 704 above substantially constant, but enough to draw pivot joint 716 downward and compress spring segments 712. Angles θ between spring segments 712 and link 718 increase, and force F between spring segments 712 at pivot joint 716 increases.

After the angles between spring segments 712 and link 718 pass 90 degrees (i.e., as an angle between opposing spring segments 712 passes 180 degrees) as shown in FIG. 15, spring segments 712 are able to expand again and push repetitive compliant mechanism 706 into the extended position, suddenly decreasing tension T on link 718. As watch band 704 continues to lengthen, tension T on link 718 gradually increases until it reaches a magnitude sufficient to draw another repetitive compliant mechanism 706 from the non-extended position to the extended position in a similar way (still an insubstantial magnitude of tension). For example, as shown in FIG. 15, ground joints 714 of a lower repetitive compliant mechanism 706 are connected to ground joints 714 of an upper repetitive compliant mechanism by ground joint links 1502, thus allowing the increasing tension to act on the upper repetitive compliant mechanism 706 to transition it from the non-extended position to the extended position.

To promote sequential, non-simultaneous opening, repetitive compliant mechanisms 706 of watch band 704 may be formed with different spring constants for their spring segments 712. While the spring constant for the pair of spring segments 712 within a given repetitive compliant mechanism may be the same to promote even opening, the spring constants of a first repetitive compliant mechanism 706 may be lower than those of a second repetitive compliant mechanism 706 spaced apart in the length direction of watch band 704, so that the first repetitive compliant mechanism 706 opens before the second repetitive compliant mechanism 706. In some embodiments there are more than two different spring constants among repetitive compliant mechanisms 706 of a single watch band 704, for example, at least five different spring constants (e.g., 10 different spring constants).

Figure 16:
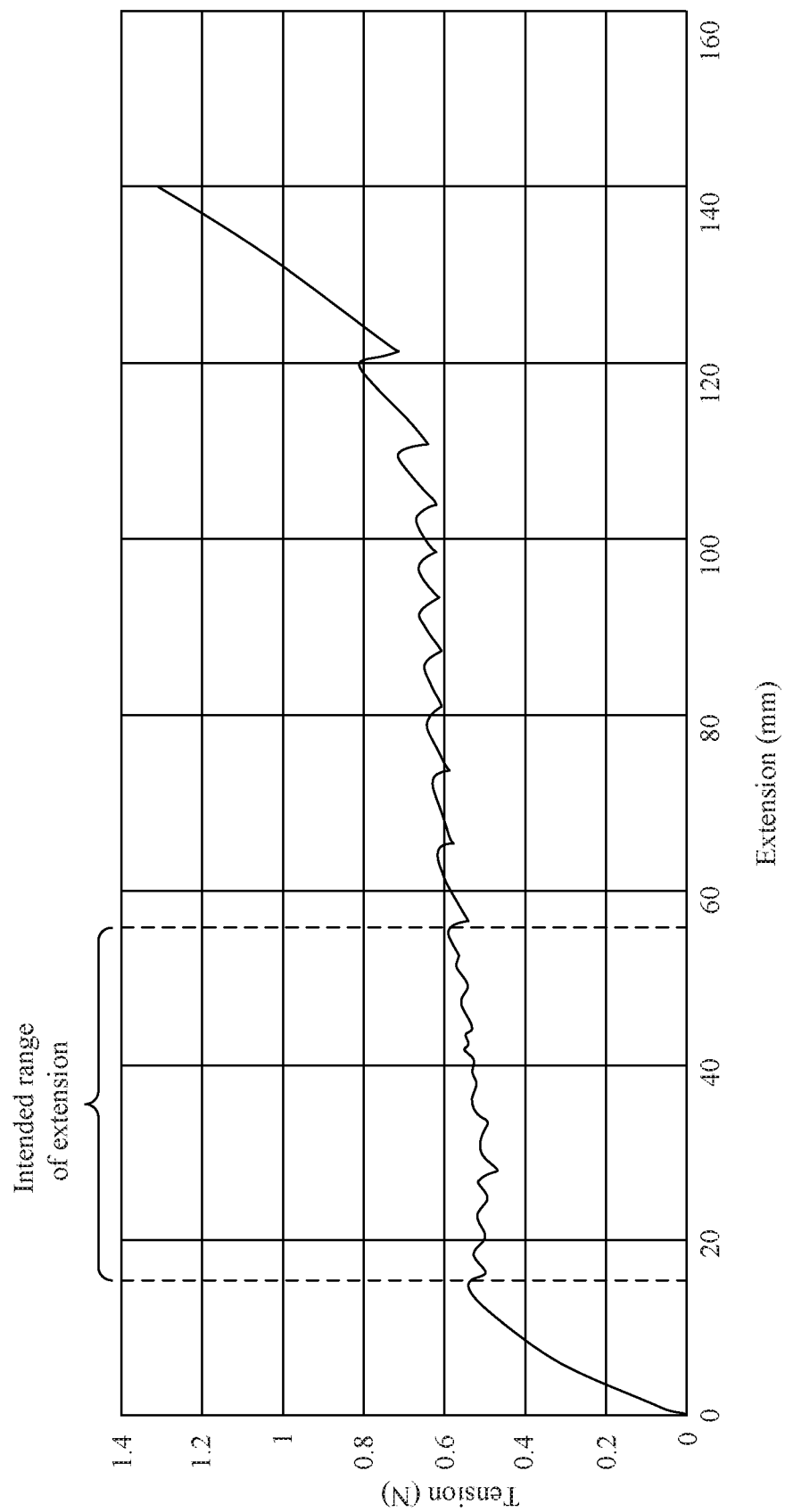
FIG. 16 shows a tension-extension curve for a watch band of FIG. 7.

As repetitive compliant mechanisms 706 open along with extension of watch band 704, the tension-extension curve of watch band 704 may resemble the graph of FIG. 16. As can be seen, within a significant intended range of extension (greater than 10-20 millimeters), tension never changes by more than 0.2 Newtons. The curve exhibits a slight "sawtooth" up-and-down pattern within that range, due to the sequential opening of repetitive compliant mechanisms 706, but the variations due to these individual openings are so small as to allow the overall tension on watch band 704 to remain substantially constant throughout the intended range of extension. The intended range of extension may include differences in circumference encompassing the range of motion of most adult human wrists (e.g., between straight and bent), possibly with additional range above and below the range of motion of most adult human wrists to accommodate those with larger- or smaller-than-normal wrists. For example, in the graph of FIG. 16, an average user must expand their watch band by say 30 millimeters from neutral (0 tension and extension) to fit it around their straight wrist, and the maximum increase in circumference for this user's wrist may be 10 millimeters, to a 40 millimeter total extension.

Since the intended range of extension begins around 15 millimeters and ends around 55 millimeters, a user with much smaller or much larger wrists, and/or with much smaller or much larger changes in circumference could also wear the same watch band and the band would maintain substantially the same tension and apply substantially the same force to each user.

Figure 17:
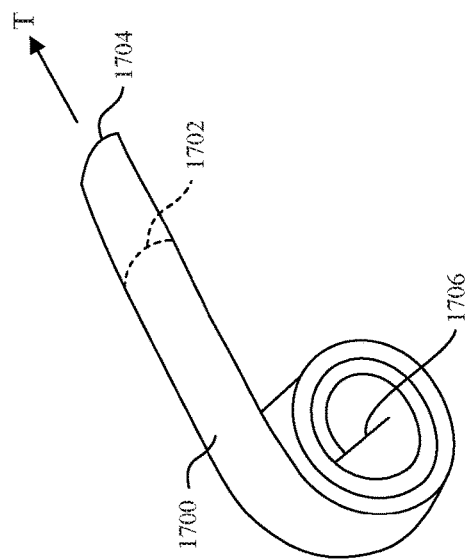
FIG. 17 shows a constant-force spring.

In some embodiments, instead of or in addition to repetitive compliant mechanisms as described above, a watch band may include a constant-force mechanism including a constant-force spring that connects band portions that are movable relative to each other via the constant-force mechanism. FIG. 17 shows an example constant-force spring 1700 such as may be used in the described embodiments. Constant force spring 1700 has been pre-tensioned and pre-shaped into a tightly wound roll that resists deflection with a substantially constant force. Thus, as constant-force spring 1700 is drawn from position 1702 to position 1704 relative to the axis 1706 of its coil under tension T, tension T remains substantially constant. The magnitude of the substantially constant tension may be adjustable by adjusting characteristics of the constant-force springs (e.g., positioning, number of coil turns), or by interchanging different constant-force springs with different characteristics. This can help watch bands provide an intended target constant force and accommodate a wide range of wrist sizes.

The overall length of the watch band (i.e., the distance between the ends of the band that connect to a watch body) can be increased or decreased by the motion of the separate band portions relative to each other, as will be described below. Constant force springs in the subsequently described embodiments may be pre-loaded to the substantially constant tension when a user expands the watch band to put it on, and may maintain the substantially constant tension within the watch band throughout motion of the user's wrist.

Figure 18:
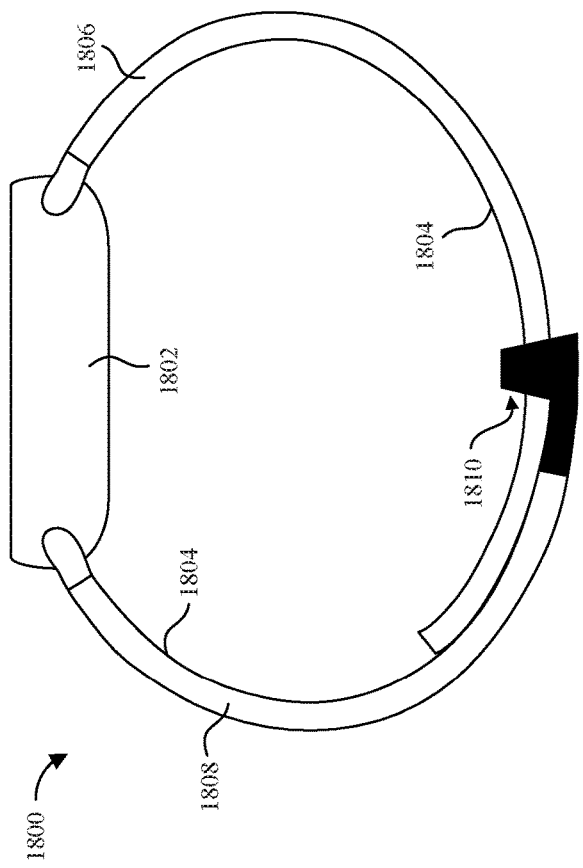
FIG. 18 shows a watch with a watch band that includes a rack-and-pinion mechanism with a constant-force spring.
Figure 19:
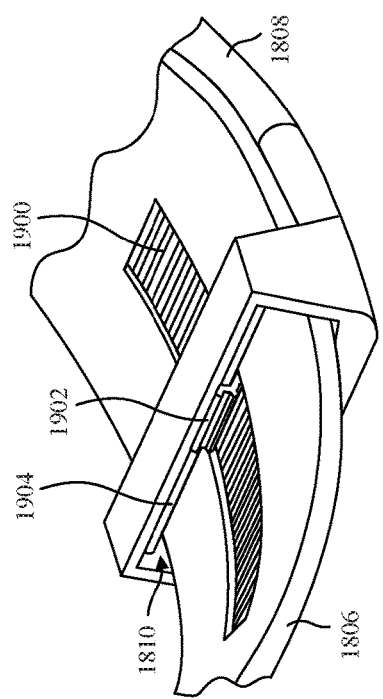
FIG. 19 shows a portion of the watch band of FIG. 18.

FIG. 18 shows a watch 1800, which includes a watch body 1802 connected to a watch band 1804. Watch band 1804 has two watch band portions, first watch band portion 1806 and second watch band portion 1808. First watch band portion 1806 extends through an opening 1810 of second watch band portion 1808. First watch band portion 1806 and second watch band portion 1808 may engage within opening 1810 by a rack-and-pinion mechanism. First watch band portion 1806 may include a rack 1900, as shown in FIG. 19. Second watch band portion 1808 may include a pinion gear 1902, which engages rack 1900. Pinion gear 1902 may rotate around an axis shaft 1904 of second watch band portion 1808 extending across opening 1810.

Figure 20:
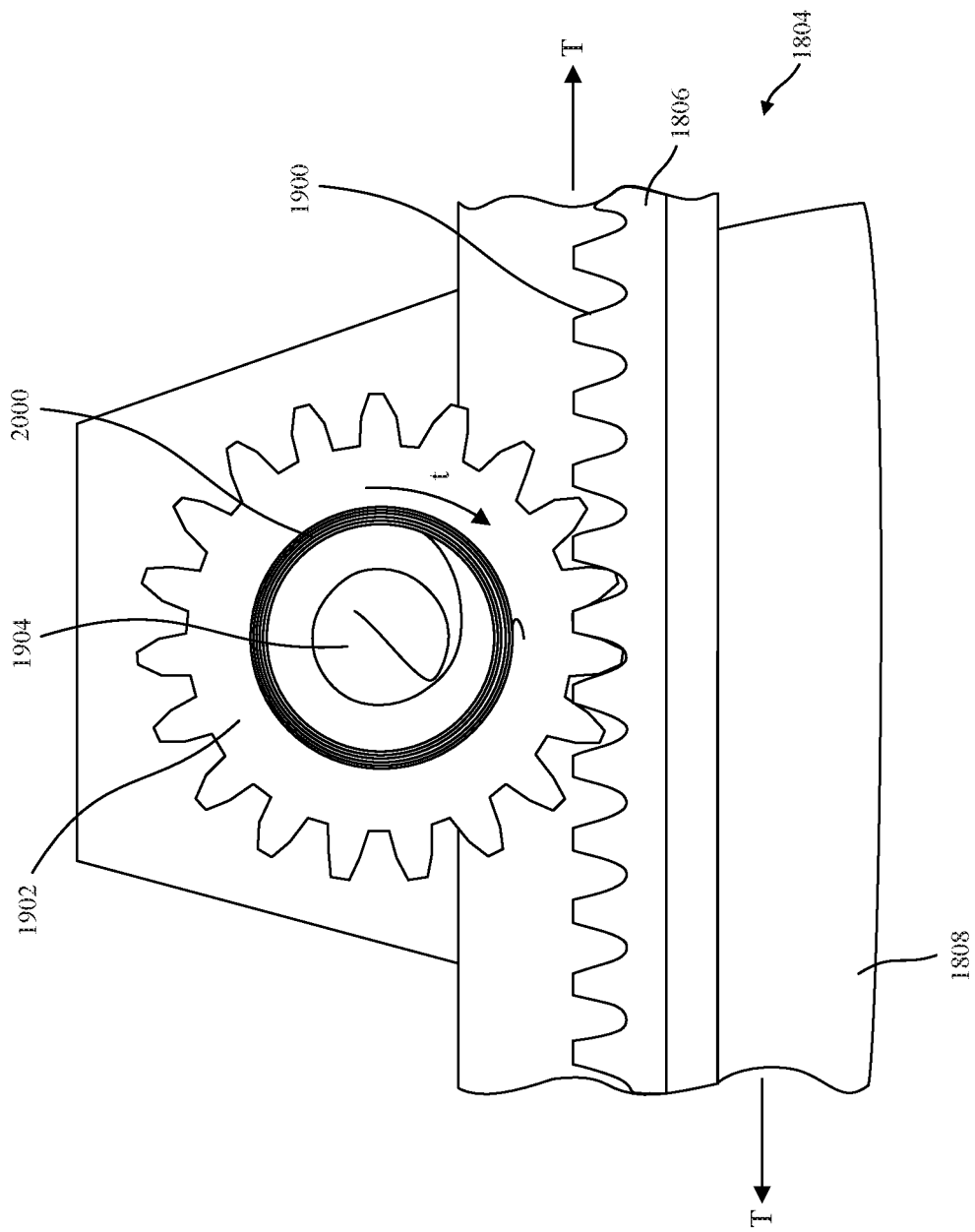
FIG. 20 shows a detailed representation of the rack-and-pinion mechanism of the watch band of FIG. 18.

FIG. 20 shows a detailed representation of rack 1900 and pinion gear 1902 of watch band 1804. Pinion gear 1902 may include a constant-force spring 2000 (e.g., a constant-torque spring, also known as a constant rotational tension spring, as shown) fixed internally to axis shaft 1904 and externally to pinion gear 1902. Constant-force spring 2000 may apply a substantially constant torque t around pinion gear 1902. Teeth of pinion gear 1902 are positioned within grooves of rack 1900, thus translational motion of watch band portions 1806 and 1808 causes rack 1900 to move relative to pinion gear 1902 and pinion gear 1902 to rotate relative to axis shaft 1904 to accommodate the motion. Throughout the motion, pinion gear 1902 maintains a substantially constant torque t around pinion gear 1902, due to its connection to constant-force spring 2000. Through the geared interconnection of first watch band portion 1806 and second watch band portion 1808 at pinion gear 1902 and rack 1900, the substantially constant torque t thus maintains a substantially constant tension T between first watch band portion 1806 and second watch band portion 1808. Thus, watch band 1804 can lengthen or shorten substantially via relative motion of rack 1900 and pinion gear 1902 while maintaining a substantially constant tension around a wearer's wrist.

Figure 22:
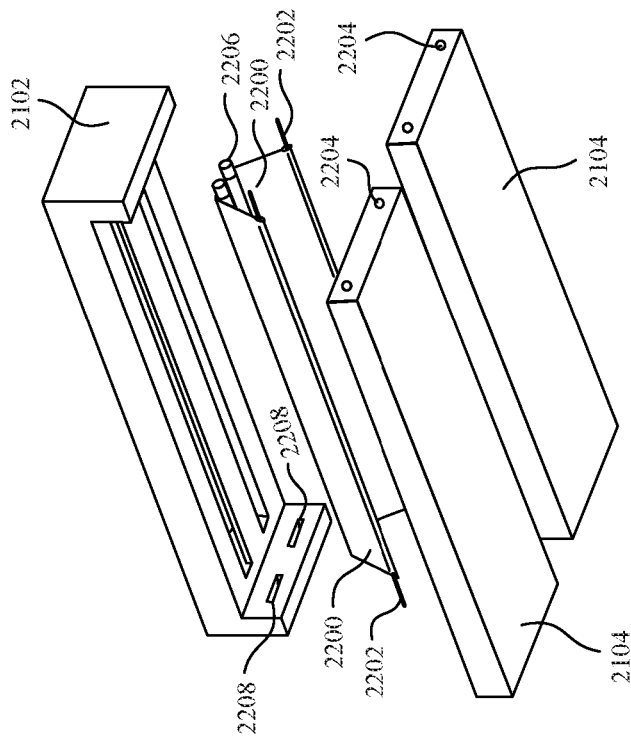
FIG. 22 shows an exploded view of a link and connectors of the watch band of FIG. 21.
Figure 21:
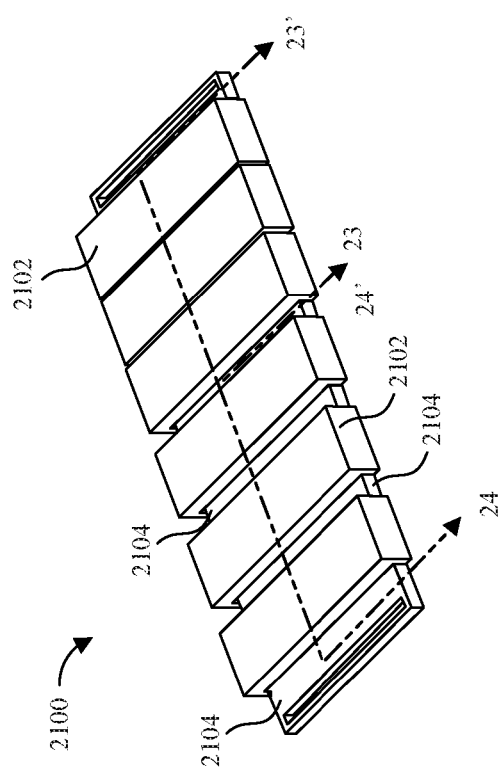
FIG. 21 shows a portion of a watch band that includes links connected by constant-force springs.

FIG. 21 shows a portion of a watch band 2100, which includes multiple links 2102 connected to each other by connectors 2104. Links 2102 can move relative to each other to allow watch band 2100 to lengthen or shorten. In FIG. 21, links 2102 on the left side have been moved away from each other in an extended configuration, exposing connectors 2104, while links on the right side remain together in a non-extended configuration. To maintain a substantially constant tension within watch band 2100, each link 2102 is connected to its adjacent connectors 2104 by a constant-force spring 2200, as shown in FIG. 22. FIG. 22 shows an exploded view of a portion of watch band 2100.

As shown in FIG. 22, each constant-force spring 2200 may extend between a link 2102 and a connector 2104. Each constant-force spring 2200 may also extend in the width direction of watch band 2100 (e.g., extending greater than 50% or 70% of the width of watch band 2100), and may extend farther in the width direction than it does between link 2102 and connector 2104. Each constant-force spring 2200 may be coiled around a shaft 2206 rotatably fixed to a link 2102, and may terminate in a shaft 2202. Shaft 2202 may be connected to an interior cavity of its corresponding connector 2104. Shafts 2202 may extend between ends of connectors 2104, in the width direction. Shafts 2202 may extend through holes 2204 of connectors 2104 and into slots 2208 of links 2102. This arrangement allows connectors 2104 to move relative to links 2102, and such motion will be limited by the corresponding motion of shafts 2202 within slots 2208. The motion of multiple links 2102 relative to their adjacent connectors 2104 allows the overall length of watch band 2100 to lengthen or shorten substantially.

Figure 24:
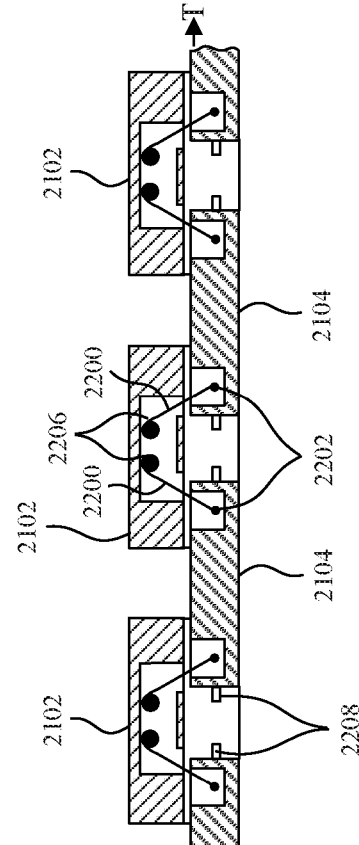
FIGS. 23 and 24 show cross sections along lines 23-23' and 24-24', respectively, of FIG. 21.
Figure 23:
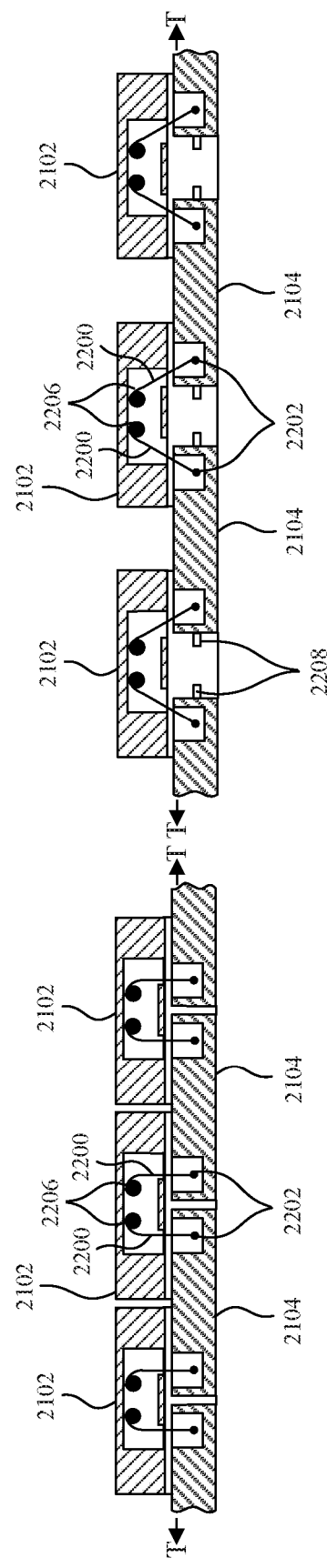

Constant force springs 2200 apply a substantially constant tension between each link 2102 and connector 2104 throughout their motion relative to each other, thereby applying a substantially constant tension to watch band 2100 overall as it lengthens and shortens. FIGS. 23 and 24 show in cross section how constant-force springs 2200 extend and contract to apply substantially constant tension. In FIG. 23 adjacent links 2102 are in a non-extended configuration, and their corresponding constant-force springs 2200 are similarly in a non-extended configuration. As links 2102 move to the extended configuration, shown in FIG. 24, constant-force springs 2200 similarly extend, and apply substantially constant tension as they do so. Thus, watch band 2100 can lengthen or shorten substantially via relative motion of links 2102 while maintaining a substantially constant tension T around a wearer's wrist.

FIG. 25 shows a cross-sectional side view of a watch 2500, which includes a watch body 2502 connected to a watch band 2504. Watch band 2504 has two watch band portions, first watch band portion 2506 and second watch band portion 2508. First watch band portion 2506 and second watch band portion 2508 are connected through an extension housing 2510. First watch band portion 2506 extends and terminates within a first opening 2512 of extension housing 2510 and second watch band portion 2508 extends and terminates within a second opening 2514 of extension housing 2510. Watch band portions 2506 and 2508 can extend within openings 2512 and 2514 to different extents. In other words, the lengths of watch band portions 2506 and 2508 within extension housing 2510 are variable. This variability allows the overall length of watch band 2504 to lengthen or shorten.

Each watch band portion 2506 and 2508 is attached to extension housing 2510 by at least one constant-force spring 2600. FIG. 26 shows extension housing 2510 with an upper portion removed, to show its interior. As shown in FIG. 26, each constant-force spring 2600 may be coiled around a shaft 2602 fixed to extension housing 2510, and may terminate at a connection with one of first watch band portion 2506 and second watch band portion 2508.

As watch band 2504 is lengthened, ends of watch band portions 2506 and 2508 move away from each other within extension housing 2510. Throughout this motion, constant-force springs 2600 maintain a substantially constant tension on watch band portions 2506 and 2508 through the connection of constant-force springs 2600 with extension housing 2510. Thus, watch band 2504 can lengthen or shorten substantially via relative motion of watch band portions 2506 and 2508 while maintaining a substantially constant tension around a wearer's wrist.

In some embodiments, extension housing 2510 is monolithic. In other embodiments, extension housing 2510 is formed of two sections 2606 and 2608 separable and attachable (e.g., along a connection interface 2604). In such separable embodiments, extension housing 2510 may act as a clasp to help a user don or doff watch 2500 by attaching or detaching sections 2606 and 2608 from each other.

In some embodiments, instead of or in addition to repetitive compliant mechanisms and constant-force mechanisms as described above, a watch band may include a constant-force compression mechanism. For example, a watch band may include a constant-force pillow or a shape-memory segment that apply substantially constant force to a user's wrist by maintaining a substantially constant tension in the watch band.

Figure 27:
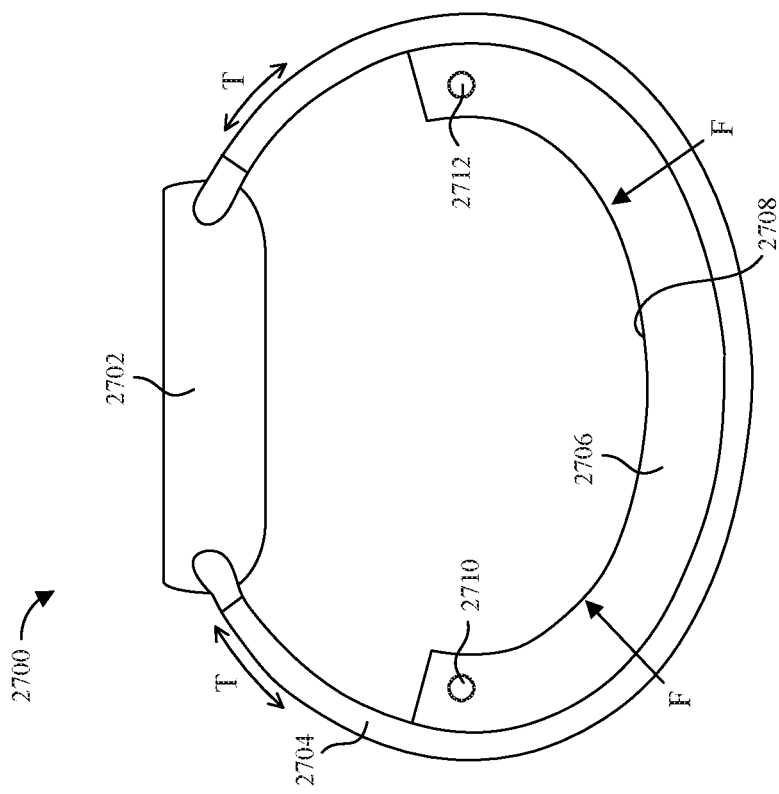
FIG. 27 shows a watch with a watch band that includes a constant-force pillow.

FIG. 27 shows a watch 2700, which includes a watch body 2702 connected to a watch band 2704. Watch band 2704 includes a constant-force pillow 2706 on an interior side of watch band 2704. When worn by a user, constant-force pillow 2706 may compress or expand as the user's wrist changes circumference. Throughout such compression and expansion, constant-force pillow 2706 may apply a substantially constant force F to the user's wrist, and thus maintain a substantially constant tension T in watch band 2704. Through the compression and expansion of constant-force pillow 2706, watch 2700 can accommodate changes in wrist circumference by correspondingly changing an interior circumference 2708 of watch band 2704, while the overall length of watch band 2704 may remain unchanged. To apply such substantially constant force to a user's wrist, constant-force pillow 2706 may be formed of constant-force foam.

In some embodiments, instead of or in addition to being formed of constant-force foam, constant-force pillow 2706 may be formed of a bladder, filled with air. Such bladder may include an air intake 2710 and an air exhaust 2712. Air exhaust 2712 may include a valve configured to exhaust air upon an increase in bladder pressure above a predetermined amount (e.g., in response to a user bending their wrist, which by increasing its circumference presses against bladder more forcefully, thereby increasing the internal pressure within the bladder). Air intake 2710 may include a valve configured to draw air into bladder upon a decrease in bladder pressure below a predetermined amount (e.g., in response to a user straightening their wrist, which by decreasing its circumference presses against bladder less forcefully, thereby decreasing the internal pressure within the bladder).

Figure 28:
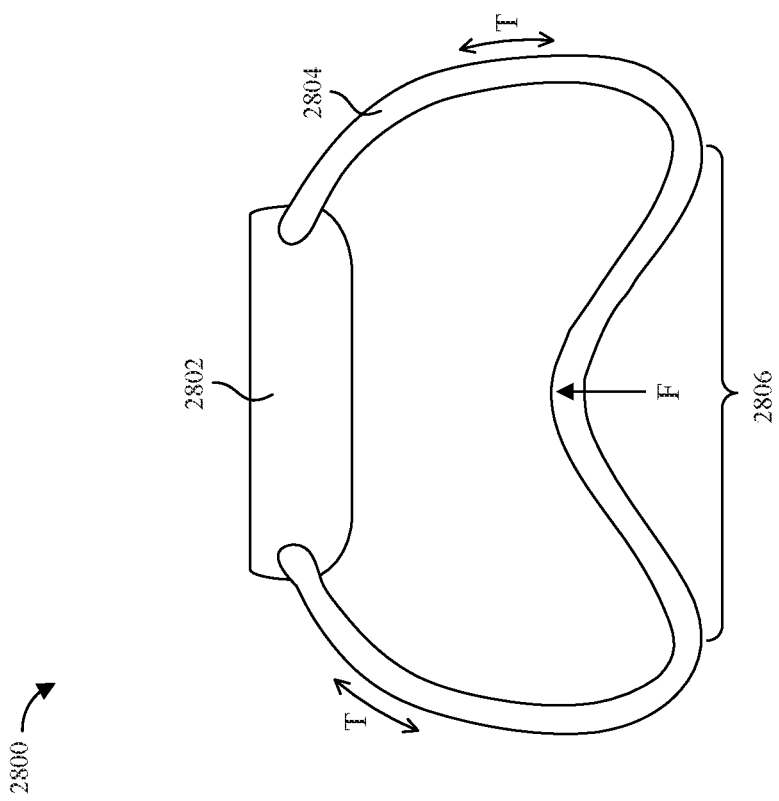
FIG. 28 shows a watch with a watch band that includes a shape-memory segment.

FIG. 28 shows a watch 2800, which includes a watch body 2802 connected to a watch band 2804. Watch band 2804 includes a shape-memory segment 2806, having a natural shape curving toward an interior of watch band 2804, within the area that a user would put their wrist. To don watch 2800, a user must deform shape-memory segment 2806 out of the way, to accommodate the user's wrist. However, shape-memory segment 2802 is biased toward its natural shape, and so presses against the user's wrist in an attempt to return to its natural shape. Due to this bias, as a user's wrist changes circumference shape-memory segment 2806 may deform more or less to accommodate the circumference, all the while maintaining a substantially constant force F on the user's wrist, and a substantially constant tension T in watch band 2804.

The foregoing descriptions of the specific embodiments described herein are presented for purposes of illustration and description. These exemplary embodiments are not intended to be exhaustive or to limit the embodiments to the precise forms disclosed. All specific details described are not required in order to practice the described embodiments.

It will be apparent to one of ordinary skill in the art that many modifications and variations are possible in view of the above teachings, and that by applying knowledge within the skill of the art, one may readily modify and/or adapt for various applications such specific embodiments, without undue experimentation, without departing from the general concept of the present invention. Such adaptations and modifications are intended to be within the meaning and range of equivalents of the disclosed embodiments, based on the teaching and guidance presented herein.

The Detailed Description section is intended to be used to interpret the claims. The Summary and Abstract sections may set forth one or more but not all exemplary embodiments of the present invention as contemplated by the inventor(s), and thus, are not intended to limit the present invention and the claims.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The phraseology or terminology used herein is for the purpose of description and not limitation, such that the terminology or phraseology of the present specification is to be interpreted by the skilled artisan.

The breadth and scope of the present invention should not be limited by any of the above-described exemplary embodiments, but should be defined in accordance with the claims and their equivalents.

What is claimed is:

1. A watch band comprising:
    a first band portion that is connectable to a first side of a watch body;
    a second band portion that is connectable to a second side of the watch body; and
    a constant-force spring connecting the first band portion to the second band portion, wherein the constant-force spring is pre-loaded to a substantially constant tension that is maintained:
        when a user expands the watch band to don the watch band on a wrist of the user; and
        when the watch band is worn throughout motion of a wrist of the user.

2. The watch band of claim 1, wherein:
    the first band portion comprises a rack; and
    the second band portion comprises a pinion gear, wherein the constant-force spring applies a substantially constant torque to the pinion gear.

3. The watch band of claim 2, wherein:
    the rack is positioned on an inner surface of the first band portion; and
    the first band portion extends through an opening of the second band portion to align the rack with the pinion gear, wherein the constant-force spring draws the first band portion into the opening of the second band portion.

4. The watch band of claim 1, wherein:
    the first band portion is a link;
    the second band portion is a connector; and
    the watch band further comprises:
        a first shaft rotatably fixed to the link, wherein the constant-force spring is coiled around the first shaft; and
        a second shaft extending through a hole of the connector and a slot of the link to slidably couple the link to the connector.

5. The watch band of claim 4, wherein:
    the first band portion is one of multiple first band portions;

the second band portion is one of multiple second band portions; and the constant-force spring is one of multiple constant-force springs, wherein each pair of adjacent first and second band portions are connected by one of the multiple constant-force springs.

6. The watch band of claim 1, further comprising:

an extension housing, wherein the first band portion and the second band portion extend within the extension housing;

wherein:
the constant-force spring is a first constant-force spring;
the first band portion is coupled to the extension housing by the first constant-force spring; and
the second band portion is coupled to the extension housing by a second constant-force spring.

7. The watch band of claim 6, wherein the extension housing comprises:

a first section receiving the first band portion; and
a second section receiving the second band portion, wherein the first section and the second section are separable from and attachable to each other by a connection interface.

8. A watch band comprising:

a first band portion that is connectable to a first side of a watch body;
a second band portion that is connectable to a second side of the watch body; and
a constant-force spring connecting the first band portion to the second band portion, wherein the constant-force spring is pre-shaped into a tightly wound roll that resists deflection with a substantially constant force.

9. The watch band of claim 8, wherein:

the first band portion comprises a rack; and
the second band portion comprises a pinion gear, wherein the constant-force spring applies a substantially constant torque to the pinion gear.

10. The watch band of claim 9, wherein:

the rack is positioned on an inner surface of the first band portion; and
the first band portion extends through an opening of the second band portion to align the rack with the pinion gear, wherein the constant-force spring draws the first band portion into the opening of the second band portion.

11. The watch band of claim 8, wherein:

the first band portion is a link;
the second band portion is a connector; and
the watch band further comprises:
  a first shaft rotatably fixed to the link, wherein the constant-force spring is coiled around the first shaft; and
  a second shaft extending through a hole of the connector and a slot of the link to slidably couple the link to the connector.

12. The watch band of claim 11, wherein:

the first band portion is one of multiple first band portions;
the second band portion is one of multiple second band portions; and
the constant-force spring is one of multiple constant-force springs, wherein each pair of adjacent first and second band portions are connected by one of the multiple constant-force springs.

13. The watch band of claim 8, further comprising:

an extension housing, wherein the first band portion and the second band portion extend within the extension housing;

wherein:
the constant-force spring is a first constant-force spring;
the first band portion is coupled to the extension housing by the first constant-force spring; and
the second band portion is coupled to the extension housing by a second constant-force spring.

14. The watch band of claim 13, wherein the extension housing comprises:

a first section receiving the first band portion; and
a second section receiving the second band portion, wherein the first section and the second section are separable from and attachable to each other by a connection interface.

15. A watch band comprising:

a first band portion that is connectable to a first side of a watch body;
a second band portion that is connectable to a second side of the watch body; and
a constant-force spring connecting the first band portion to the second band portion, wherein the constant-force spring is coiled about an axis and provides tension that is substantially constant as the constant-force spring transitions between:
  a first position with a first number of turns about the axis; and
  a second position with a second number of turns about the axis.

16. The watch band of claim 15, wherein:

the first band portion comprises a rack; and
the second band portion comprises a pinion gear, wherein translational motion of the rack causes the pinion gear to rotate about a shaft, such that, while the constant-force spring provides the tension that is substantially constant, the constant-force spring further applies a substantially constant torque to the pinion gear.

17. The watch band of claim 16, wherein:

the rack is positioned on an inner surface of the first band portion; and
the first band portion extends through an opening of the second band portion to align the rack with the pinion gear, wherein the constant-force spring draws the first band portion into the opening of the second band portion.

18. The watch band of claim 15, wherein:

the first band portion is a link;
the second band portion is a connector; and
the watch band further comprises:
  a first shaft rotatably fixed to the link, wherein the constant-force spring is coiled around the first shaft; and
  a second shaft extending through a hole of the connector and a slot of the link to slidably couple the link to the connector.

19. The watch band of claim 18, wherein:

the first band portion is one of multiple first band portions;
the second band portion is one of multiple second band portions; and
the constant-force spring is one of multiple constant-force springs, wherein each pair of adjacent first and second band portions are connected by one of the multiple constant-force springs.

20. The watch band of claim 15, further comprising:

an extension housing, wherein the first band portion and the second band portion extend within the extension housing;

wherein:
the constant-force spring is a first constant-force spring;

the first band portion is coupled to the extension housing by the first constant-force spring; and
the second band portion is coupled to the extension housing by a second constant-force spring;
the extension housing comprises:
 a first section receiving the first band portion; and
 a second section receiving the second band portion, wherein the first section and the second section are separable from and attachable to each other by a connection interface.

* * * * *